United States Patent
Kropf et al.

(10) Patent No.: US 11,702,616 B2
(45) Date of Patent: Jul. 18, 2023

(54) METAL COMPLEXES AND DISHWASHING DETERGENTS CONTAINING THEM

(71) Applicant: Henkel AG & Co. KGaA, Duesseldorf (DE)

(72) Inventors: Christian Kropf, Hilden (DE); Sebastian Polarz, Wedemark (DE); Marvin Lionel Frisch, Berlin (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 51 days.

(21) Appl. No.: 17/186,406

(22) Filed: Feb. 26, 2021

(65) Prior Publication Data
US 2021/0269746 A1 Sep. 2, 2021

(30) Foreign Application Priority Data

Feb. 27, 2020 (DE) .......... 102020202492.8
Jun. 24, 2020 (DE) .......... 102020207791.6

(51) Int. Cl.
| C11D 7/02 | (2006.01) |
| C11D 7/32 | (2006.01) |
| C11D 7/34 | (2006.01) |
| C11D 3/16 | (2006.01) |
| C11D 3/20 | (2006.01) |
| C11D 3/28 | (2006.01) |
| C11D 11/00 | (2006.01) |
| C11D 3/39 | (2006.01) |

(52) U.S. Cl.
CPC ........ *C11D 3/168* (2013.01); *C11D 3/2096* (2013.01); *C11D 3/28* (2013.01); *C11D 3/3915* (2013.01); *C11D 3/3917* (2013.01); *C11D 7/34* (2013.01); *C11D 11/0023* (2013.01)

(58) Field of Classification Search
CPC ........ C11D 3/3915; C11D 3/3917; C11D 7/34
USPC ................. 510/220, 221, 376, 492
See application file for complete search history.

(56) References Cited

U.S. PATENT DOCUMENTS

| 6,340,661 B1 * | 1/2002 | van Deurzen ....... C11D 3/3932 510/276 |
| 6,479,447 B2 * | 11/2002 | Bijl ................ C11D 1/82 510/303 |
| 8,889,611 B2 * | 11/2014 | Reinhardt ........ C11D 17/0052 510/357 |

FOREIGN PATENT DOCUMENTS

WO 2016062784 A1 4/2016

OTHER PUBLICATIONS

Zech, Stephan G. et al., "Probing the Water Coordination of Protein-Targeted MRI Contrast Agents by Pulsed ENDOR Spectroscopy", ChemPhysChem, Nov. 2005, vol. 6, pp. 2570-2577, Wiley-VCH Verlag GmbH & Co. KGaA, Weinheim. DOI: 10.1002/cphc.200500250.

Chang John Yu-Chih et al., "Syntheses of 8-Quinolinolatocobalt(III) Complexes Containing Cyclen Based Auxiliary Ligands as Models for Hypoxia-Activated Prodrugs", The Royal Society of Chemistry: Dalton Transactions, Nov. 2010, vol. 39, p. 11535-11550. DOI: 10.1039/c0dt01142h.

Jagadish, Bhumasamudram et al.,"On the Synthesis of 1,4,7-tris(tert-butoxycarbonylmthyl)-1,4,7,10-tetraazacyclododecane", Tetrahedron Letters, 2011, vol. 52, pp. 2058-2061, Elsevier Ltd. DOI:10.1016/j.tetlet.2010.10.074.

DE Search Report 10 2020 202 492.8 Completed: Oct. 27, 2020; dated Oct. 27, 2020 8 pages.

* cited by examiner

*Primary Examiner* — Gregory R Delcotto
(74) *Attorney, Agent, or Firm* — Bojuan Deng

(57) ABSTRACT

The invention relates to compounds of general formula (I),

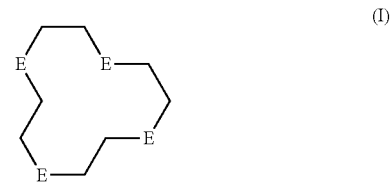

(I)

in which each E independently represents O or $NR^1$, with the proviso that at least 1 E is not O and at least 1 $R^1$ represents a substituted $C_{1-22}$ alkyl of the general formula (IIa) or (IIb) or (IIIa) or (IIIb),

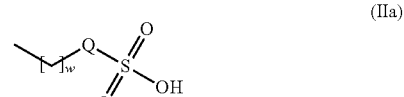

(IIa)

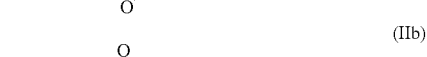

(IIb)

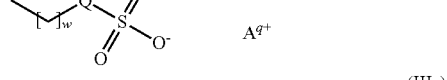

(IIIa)

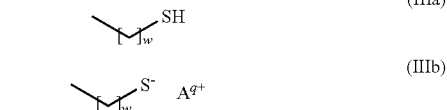

(IIIb)

in which Q represents O or $CH_2$, w represents a number from 1 to 22, q represents 1 or 2 and $A^+$ represents a cation selected from alkali metal cations where q=1, ½ alkaline earth cations where q=2 and ammonium ions where q=1, as well as metal complexes having this ligand compound and dishwashing detergents which contain such metal complexes.

10 Claims, No Drawings

METAL COMPLEXES AND DISHWASHING DETERGENTS CONTAINING THEM

FIELD OF THE INVENTION

The present invention relates to cleaning-enhancing metal complexes, the cyclic ligands thereof, an automatic dishwashing detergent which, due to the concentration of such complexes, shows improved cleaning performance in removing burnt-in soiling, the use of this dishwashing detergent and a method for automatic dishwashing using this dishwashing detergent.

BACKGROUND OF THE INVENTION

The most important criterion in automatic dishwashing is the cleaning performance on a wide variety of soiling, which is often brought into the dishwasher in the form of food residues. Especially in the case of stubborn stains, such as those that occur when preparing foods having proteins and starches at high temperatures (roasting, baking, deep-frying, browning, etc.), so-called burnt-in soiling, the cleaning performance of available dishwashing detergents remains unsatisfactory. Insufficient cleaning performance leads to consumer dissatisfaction. There is therefore a general need for automatic dishwashing detergents which have good cleaning performance even with burnt-in soiling.

International patent application WO 2016/062784 A1 discloses cleaning-enhancing N-substituted 1,4,7,10-tetraazacyclododecanes.

BRIEF SUMMARY OF THE INVENTION

It has now been found, surprisingly, that metal complexes with certain heterocyclic ligands, which have sulfo or sulfato or thioalkyl substituents on the hetero atom, bring about improved cleaning performance on burnt-in soiling when used in dishwashers.

A first aspect of the present invention relates to a compound of the general formula (I),

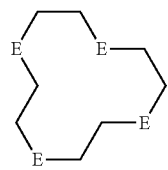

(I)

in which each E independently represents O or $NR^1$, with the proviso that at least 1 E is not O, each $R^1$ independently represents H, unsubstituted or substituted, linear or branched $C_{1-22}$ alkyl, unsubstituted or substituted, linear or branched $C_{1-22}$ heteroalkyl, unsubstituted or substituted aryl, unsubstituted or substituted heteroaryl, unsubstituted or substituted, linear or branched $C_{2-20}$ alkenyl, unsubstituted or substituted, linear or branched $C_{2-20}$ alkynyl, unsubstituted or substituted, linear or branched $C_{2-20}$ heteroalkenyl, unsubstituted or substituted, linear or branched alkylaryl, or unsubstituted or substituted, linear or branched alkylheteroaryl, with the proviso that at least 1 $R^1$ represents a substituted $C_{1-22}$ alkyl of the general formula (IIa) or (IIb), or with the proviso that at least 1 $R^1$ is a substituted $C_{1-22}$ alkyl of the general formula (IIIa) or (IIIb),

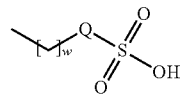
(IIa)

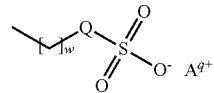
(IIb)

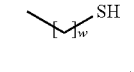
(IIIc)

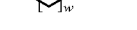
(IIId)

in which Q represents O or $CH_2$, w represents a number from 1 to 22, q represents 1 or 2 and $A^+$ represents a cation selected from alkali metal cations where q=1, ½ alkaline earth cations where q=2 and ammonium ions where q=1.

Preferably 1, in particular 2, particularly preferably 3 or 4 of the Es are not O. Preferably w represents a number from 2 to 20, in particular from 3 to 18.

In the general formula (I), 1 group $R^1$ preferably corresponds to the general formula (IIa), (IIb), (IIIa) or (IIIb), wherein mixtures of compounds with $R^1$=IIa and $R^1$=IIb and mixtures of compounds with $R^1$=IIIa and $R^1$=IIIb are possible without restriction and correspond to the partial salt formation from compounds with $R^1$=IIa and $R^1$=IIIa. The groups $R^1$ which do not correspond to the general formula (IIa), (IIb), (IIIa) or (IIIb) are preferably selected from

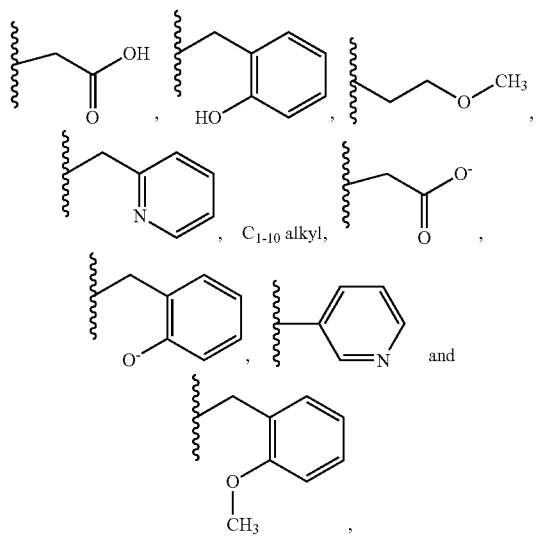

wherein the anions shown are brought to charge neutrality by the presence of a cation $A^{q+}$ defined above.

Another object of the invention is a metal complex of the general formula (III),

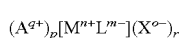  (III)

in which q represents 1 or 2 and $A^+$ represents a cation selected from alkali metal cations where q=1, ½ alkaline earth cations where q=2 and ammonium ions where q=1, $M^{n+}$ represents an aluminum ion, a transition metal ion or a lanthanoid metal ion, L represents a ligand of the formula (I)

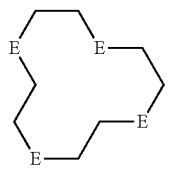

(I)

in which each E independently represents O or $NR^1$, with the proviso that at least 1 E is not O, each $R^1$ independently represents H, unsubstituted or substituted, linear or branched $C_{1-22}$ alkyl, unsubstituted or substituted, linear or branched $C_{1-22}$ heteroalkyl, unsubstituted or substituted aryl, unsubstituted or substituted heteroaryl, unsubstituted or substituted, linear or branched $C_{2-20}$ alkenyl, unsubstituted or substituted, linear or branched $C_{2-20}$ alkynyl, unsubstituted or substituted, linear or branched $C_{2-20}$ heteroalkenyl, unsubstituted or substituted, linear or branched alkylaryl, or unsubstituted or substituted, linear or branched alkylheteroaryl, with the proviso that at least 1 $R^1$ represents a substituted $C_{1-22}$ alkyl of the general formula (IIa) or (IIc), or with the proviso that at least 1 $R^1$ represents a substituted $C_{1-22}$ alkyl of the general formula (IIIa) or (IIIc),

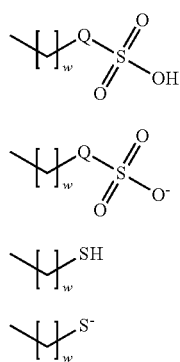

in which Q represents O or $CH_2$, w represents a number from 1 to 22, q represents 1 or 2 and $A^+$ represents a cation selected from alkali metal cations where q=1, ½ alkaline earth cations where q=2 and ammonium ions where q=1, $X^{o-}$ represents an anion selected from $F^-$, $Cl^-$, $Br^-$, $I^-$, $OH^-$, $HSO_3^-$, $SO_3^{2-}$, $SO_4^{2-}$, $HSO_4^-$, $NO_2^-$, $NO_3^-$, $PO_4^{3-}$, $HPO_4^{2-}$, $H_2PO_4^-$, $BF_4^-$, $PF_6^-$, $ClO_4^-$, acetate, citrate, formate, glutarate, lactate, malate, malonate, oxalate, pyruvate, tartrate, methanesulfonate, methyl sulfate, p-toluenesulfate and succinate, n is a number from 1 to 5, m is a number from 0 to 4 and o is a number from 1 to 3 and p and r independently of one another represent a number from 0 and 7, with the proviso that the sum of n and the product of p and q is equal to the sum of m and the product of r and o.

As is well known, not every number from the range defined for n is suitable for every metal, because metals from group 3 of the periodic table of elements are normally present in the oxidation state +3, metals from group 4, group 7, group 8, group 9, group 10 and the lanthanide metals in oxidation states +2, +3 or +4, metals from group 5 in oxidation states +2, +3, +4 or +5, metals from group 6 in oxidation states +2 or +3, metals from group 11 in the +1, +2 or +3 oxidation states, metals from group 12 in the +1 or +2 oxidation state, and Al in the oxidation state +3. Preferred metal ions $M^{n+}$ are $Al^{3+}$, $Ti^{4+}$, $Y^{3+}$, $Zr^{4+}$, $La^{3+}$, $Ce^{3+}$, $Ce^{4+}$, $Sc^{3+}$, $Yb^{3+}$, $Ta^{5+}$ and mixtures thereof.

The invention also relates to a dishwashing detergent, in particular an automatic dishwashing detergent, comprising a metal complex of the formula (III) defined above.

The present invention also relates to the use of a metal complex of the formula (III) defined above or of a dishwashing detergent according to the invention in an automatic dishwashing method, in particular the use to improve the cleaning performance in an automatic dishwasher.

Yet another subject matter of the invention is an automatic dishwashing method in which a metal complex of the formula (III) defined above or a dishwashing detergent according to the invention is used, in particular for the purpose of improving the cleaning performance.

DETAILED DESCRIPTION OF THE INVENTION

The particular or preferred embodiments described above and below for the individual subjects of the invention also apply to the other subjects of the invention.

The agents according to the invention contain, based on the total weight of the agent, preferably 0.001 wt. % wt. % to 10 wt. % wt. %, in particular 0.01 wt. % wt. % to 3 wt. % wt. % of a metal complex of the formula (III) defined above and may contain, in addition to the complex essential to the invention, further constituents typically contained in such agents, preferably selected from surfactants, in particular non-ionic surfactants and/or anionic surfactants, builders, enzymes, thickeners, sequestering agents, electrolytes, corrosion inhibitors, in particular silver protectants, glass corrosion inhibitors, foam inhibitors, dyes, fragrances, bitter substances, antimicrobial agents and disintegration aids, in particular surfactant.

The agents preferably contain at least non-ionic surfactant. All non-ionic surfactants that are known to a person skilled in the art can be used as non-ionic surfactants. Suitable non-ionic surfactants include alkyl glycosides of general formula $RO(G)_x$, for example, in which R corresponds to a primary straight-chain or methyl-branched aliphatic radical, in particular an aliphatic radical that is methyl-branched in the 2 position, having 8 to 22, preferably 12 to 18, C atoms, and G is the symbol that represents a glycose unit having 5 or 6 C atoms, preferably glucose. The degree of oligomerization x, which indicates the distribution of monoglycosides and oligoglycosides, is any number between 1 and 10; x is preferably between 1.2 and 1.4. Non-ionic surfactants of the aminoxide type, for example N-cocoalkyl-N,N-dimethylamine oxide and N-tallow-alkyl-N,N-dihydroxyethylamine oxide, and of the fatty acid alkanolamides may also be suitable. The quantity of these non-ionic surfactants is preferably no more than that of the ethoxylated fatty alcohols, in particular no more than half thereof. Other suitable surfactants are the polyhydroxy fatty acid amides, which are known as PHFAs. Preferably, low-foaming non-ionic surfactants are used, in particular alkoxylated, especially ethoxylated, low-foaming non-ionic surfactants. Particularly preferably, the automatic dishwashing detergents contain non-ionic surfactants from the group of alkoxylated alcohols. One class of usable non-ionic surfactants, which can be used either as the sole non-ionic surfactant or in combination with other non-ionic surfactants, are thus alkoxylated, preferably ethoxylated or ethoxylated and propoxylated, fatty acid alkyl esters, preferably having 1 to 4 carbon atoms in the alkyl chain. Surfactants that are preferably used come from the groups of ethoxylated primary alcohols and mixtures of these surfactants with structurally complex surfactants such as polyoxypropylene/polyoxyethylene/polyoxypropylene ((PO/EO/PO) surfactants). Such (PO/EO/PO) non-ionic surfactants are characterized by good foam control. Non-ionic surfactants with alternating ethylene oxide and alkylene oxide units can be preferred. Among these, in turn, surfactants having EO-AO-EO-AO blocks are preferred, wherein one to ten EO or AO groups are bonded to one another before a block from each of the other groups follows. Here, non-ionic surfactants of the general formula

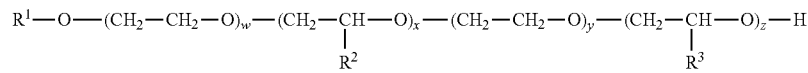

are preferred, in which $R^1$ represents a straight-chain or branched, saturated or mono- or polyunsaturated $C_{6-24}$ alkyl or alkenyl radical; each $R^2$ or $R^3$ group is selected, independently of one another, from —$CH_3$, —$CH_2CH_3$, —$CH_2CH_2$—$CH_3$, —$CH(CH_3)_2$, and the indices w, x, y, z, independently of one another, represent integers from 1 to 6. Thus, non-ionic surfactants are particularly preferred which have a $C_{9-15}$-alkyl radical with 1 to 4 ethylene oxide units, followed by 1 to 4 propylene oxide units, followed by 1 to 4 ethylene oxide units, followed by 1 to 4 propylene oxide units. Preferred non-ionic surfactants in this case are those of general formula

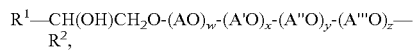

in which $R^1$ represents a straight-chain or branched, saturated or mono- or polyunsaturated $C_{6-24}$-alkyl or -alkenyl radical; $R^2$ represents H or a linear or branched hydrocarbon radical having 2 to 26 carbon atoms; A, A', A" und A'" independently of one another represent a radical from the group —$CH_2CH_2$, —$CH_2CH_2$—$CH_2$, —$CH_2$—$CH(CH_3)$, —$CH_2$—$CH_2$—$CH_2$—$CH_2$, —$CH_2$—$CH(CH_3)$—$CH_2$—, —$CH_2$—$CH(CH_2$—$CH_3)$, and w, x, y and z represent values between 0.5 and 120, where x, y and/or z can also be 0. Particularly preferred are end-capped, poly(oxyalkylated) non-ionic surfactants which, according to the formula $R^1O[CH_2CH_2O]_xCH_2CH(OH)R^2$, also comprise, in addition to a radical $R^1$, which represents linear or branched, saturated or unsaturated, aliphatic or aromatic hydrocarbon radicals having 2 to 30 carbon atoms, preferably having 4 to 22 carbon atoms, a linear or branched, saturated or unsaturated, aliphatic or aromatic hydrocarbon radical $R^2$ having 1 to 30 carbon atoms, wherein x represents values between 1 and 90, preferably values between 30 and 80, and in particular values between 30 and 60. Surfactants of the formula $R^1O[CH_2CH(CH_3)O]_x[CH_2CH_2O]_yCH_2CH(OH)R^2$ are particularly preferred, in which $R^1$ represents a linear or branched aliphatic hydrocarbon radical having 4 to 18 carbon atoms or mixtures thereof, $R^2$ represents a linear or branched hydrocarbon radical having 2 to 26 carbon atoms or mixtures thereof, and x represents values between 0.5 and 1.5, and y represents a value of at least 15. The group of these non-ionic surfactants includes, for example, the $C_{2-26}$ fatty alcohol-$(PO)_1$-$(EO)_{15-40}$-2-hydroxyalkyl ethers, in particular also the $C_{8-10}$ fatty alcohol-$(PO)_1$-$(EO)_{22}$-2-hydroxydecyl ethers. Particularly preferred are also end-capped poly(oxyalkylated) non-ionic surfactants of the formula $R^1O[CH_2CH_2O]_x[CH_2CH(R^3)O]_yCH_2CH(OH)R^2$, in which $R^1$ and $R^2$ represent, independently of one another, a linear or branched, saturated or mono- or polyunsaturated hydrocarbon radical having 2 to 26 carbon atoms, $R^3$ is independently selected from —$CH_3$, —$CH_2CH_3$, —$CH_2CH_2$—$CH_3$, —$CH(CH_3)_2$, but preferably represents —$CH_3$, and x and y represent, independently of one another, values between 1 and 32, wherein non-ionic surfactants having $R^3$=—$CH_3$ and values for x from 15 to 32 and for y from 0.5 and 1.5 are very particularly preferred. Further non-ionic surfactants that can preferably be used are the end-capped poly(oxyalkylated) non-ionic surfactants of the formula $R^1O[CH_2CH(R^3)O]_x[CH_2]_kCH(OH)[CH_2]_jOR^2$, in which $R^1$ and $R^2$ represent linear or branched, saturated or unsaturated, aliphatic or aromatic hydrocarbon radicals having 1 to 30 carbon atoms, $R^3$ represents H or a methyl, ethyl, n-propyl, iso-propyl, n-butyl, 2-butyl or 2-methyl-2-butyl radical, x represents values between 1 and 30, and k and j represent values between 1 and 12, preferably between 1 and 5. If the value x is greater than or equal to 2, each $R^3$ in the above formula $R^1O[CH_2CH(R^3)O]_x[CH_2]_kCH(OH)[CH_2]_jOR^2$ can be different. $R^1$ and $R^2$ are preferably linear or branched, saturated or unsaturated, aliphatic or aromatic hydrocarbon radicals having 6 to 22 carbon atoms, wherein radicals having 8 to 18 C atoms are particularly preferred. For the radical $R^3$, H, —$CH_3$ or —$CH_2CH_3$ are particularly preferred. Particularly preferred values for x are in the range of from 1 to 20, in particular from 6 to 15. Each $R^3$ can be different if x≥2. In this way, the alkylene oxide unit in square brackets can be varied. For example, if x represents 3, the radical $R^3$ can be selected in order to form ethylene oxide ($R^3$=H) or propylene oxide ($R^3$=$CH_3$) units, which can be joined together in any sequence, for example (EO)(PO)(EO), (EO)(EO)(PO), (EO)(EO)(EO), (PO)(EO)(PO), (PO)(PO)(EO), and (PO)(PO)(PO). The value 3 for x has been selected here as an example and can by all means be greater, wherein the range of variation increases as the values for x increase and includes a large number of (EO) groups combined with a small number of (PO) groups, for example, or vice versa. Particularly preferred end-capped poly(oxyalkylated) alcohols of the above formula have values of k=1 and j=1, and therefore the previous formula is simplified to $R^1O[CH_2CH(R^3)O]_xCH_2CH(OH)CH_2OR^2$. In the aforementioned formula, $R^1$, $R^2$ and $R^3$ are as defined above and x represents numbers from 1 to 30, preferably 1 to 20, and in particular 6 to 18. Surfactants in which the radicals $R^1$ and $R^2$ have 9 to 14 C atoms, $R^3$ represents H, and x assumes values from 6 to 15 are particularly preferred. Finally, the non-ionic surfactants of the general formula $R^1$—$CH(OH)CH_2O$-$(AO)_w$—$R^2$, in which $R^1$ represents a straight-chain or branched, saturated or mono- or polyunsaturated $C_{6-24}$-alkyl or -alkenyl radical have proven to be particularly effective; $R^2$ represents a linear or branched hydrocarbon radical having 2 to 26 carbon atoms; A represents a radical from the group $CH_2CH_2$, $CH_2CH_2CH_2$, $CH_2CH(CH_3)$, preferably $CH_2CH_2$, and w represents values between 1 and 120, preferably 10 to 80, in particular 20 to 40. The group of these non-ionic surfactants includes, for example, $C_{4-22}$ fatty alcohol-$(EO)_{10-80}$-2-hydroxyalkyl ethers, in particular also $C_{8-12}$ fatty alcohol-$(EO)_{22}$-2-hydroxydecyl ethers and $C_{4-22}$ fatty alcohol-$(EO)_{40-80}$-2-hydroxyalkyl ethers. In various embodiments of the invention, instead of the end-capped hydroxy mixed ethers, it is also possible to use the corresponding non-end-capped hydroxy mixed ethers. These can satisfy the above formulas, but where $R^2$ is hydrogen and $R^1$, $R^3$, A, A', A'', A''', w, x, y and z are as defined above.

The agents described herein, which comprise at least one non-ionic surfactant, preferably a non-ionic surfactant from the group of hydroxy mixed ethers, contain the surfactant in various embodiments in an amount based on the total weight of the agent of at least 2 wt. % wt. %, preferably at least 5 wt. % wt. %. The absolute amounts used per application can, for example, be in the range from 0.5 g to 10 g per application, preferably in the range from 1 g to 5 g per application.

All anionic surface-active substances are suitable for use as anionic surfactants in dishwashing detergents. They are characterized by a water-solubilizing anionic group, such as a carboxylate, sulfate, sulfonate, or phosphate group, and a lipophilic alkyl group having approximately 8 to 30 C atoms. In addition, glycol ether or polyglycol ether groups, ester, ether and amide groups, and hydroxyl groups can be contained in the molecule. Suitable anionic surfactants are preferably present in the form of sodium, potassium and ammonium and mono-, di- and trialkanolammonium salts having 2 to 4 carbon atoms in the alkanol group. Preferred anionic surfactants are alkyl sulfates, alkyl polyglycol ether sulfates, and ether carboxylic acids with 10 to 18 C atoms in the alkyl group and up to 12 glycol ether groups in the molecule. The dishwashing detergents therefore contain in various embodiments at least one surfactant of the formula $R^4$—O-(AO)$_n$—SO$_3^-$X$^+$. In this formula, $R^4$ represents a linear or branched, substituted or unsubstituted alkyl, aryl or alkylaryl radical, preferably a linear, unsubstituted alkyl radical, particularly preferably a fatty alcohol radical. Preferred radicals $R^1$ are selected from decyl, undecyl, dodecyl, tridecyl, tetradecyl, pentadecyl, hexadecyl, heptadecyl, octadecyl, nonadecyl, eicosyl radicals and mixtures thereof, wherein the representatives having an even number of C atoms are preferred. Particularly preferred radicals $R^1$ are derived from $C_{12}$-$C_{18}$ fatty alcohols, for example from coconut fatty alcohol, tallow fatty alcohol, lauryl, myristyl, cetyl or stearyl alcohol or from $C_{10}$-$C_{20}$ oxo alcohols. AO represents an ethylene oxide (EO) or propylene oxide (PO) group, preferably an ethylene oxide group. The index n represents an integer from 1 to 50, preferably from 1 to 20, and in particular from 2 to 10. Very particularly preferably, n represents the numbers 2, 3, 4, 5, 6, 7 or 8. X represents a monovalent cation or the nth part of an n-valent cation, the alkali metal ions being preferred, and of those Na$^+$ or K$^+$, wherein Na$^+$ is most preferred. Further cations X$^+$ may be selected from NH$_4^+$, ½Zn$^{2+}$, ½Mg$^{2+}$, ½Ca$^{2+}$, ½Mn$^{2+}$, and mixtures thereof. Particularly preferred anionic surfactants are selected from fatty alcohol ether sulfates of the formula A-1

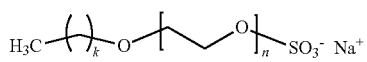

(A-1)

where k=11 to 19, and n=2, 3, 4, 5, 6, 7 or 8. Very particularly preferred representatives are Na—$C_{12-14}$ fatty alcohol ether sulfates with 2 EO (k=11-13, n=2 in formula A-1). The agents can also additionally or alternatively contain at least one surfactant of the formula $R^5$-A-SO$_3^-$Y$^+$ (A-2). In this formula A-2, $R^5$ represents a linear or branched, substituted or unsubstituted alkyl, aryl or alkylaryl radical and the group -A- represents —O— or a chemical bond. In other words, the above formula can describe sulfate surfactants (A=O) or sulfonate surfactants (A=chemical bond). Depending on the selection of the group A, specific radicals $R^5$ are preferred. In the sulfate surfactants (A=O), $R^5$ preferably represents a linear, unsubstituted alkyl radical, particularly preferably a fatty alcohol radical. Preferred radicals $R^5$ are selected from decyl, undecyl, dodecyl, tridecyl, tetradecyl, pentadecyl, hexadecyl, heptadecyl, octadecyl, nonadecyl and eicosyl radicals and mixtures thereof, wherein the representatives having an even number of C atoms are preferred. Particularly preferred radicals $R^5$ are derived from $C_{12}$-$C_{18}$ fatty alcohols, for example from coconut fatty alcohol, tallow fatty alcohol, lauryl, myristyl, cetyl or stearyl alcohol or from $C_{10}$-$C_{20}$ oxo alcohols. Y represents a monovalent cation or the nth part of an n-valent cation, the alkali metal ions, including Na$^+$ or K$^+$, being preferred in this case, wherein Na$^+$ is most preferred. Further cations Y+ may be selected from NH$_4^+$, ½Zn$^{2+}$, ½Mg$^{2+}$, ½Ca$^{2+}$, ½Mn$^{2+}$, and mixtures thereof. Particularly preferred surfactants of this kind are selected from fatty alcohol sulfates of formula

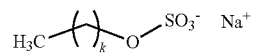

where k=11 to 19. Very particularly preferred representatives are Na—$C_{12-14}$ fatty alcohol sulfates (k=11-13). In the sulfonate surfactants (A=chemical bond in formula A-2), $R^5$ preferably represents a linear or branched unsubstituted alkylaryl radical. Here, too, X represents a monovalent cation or the nth part of an n-valent cation, in this case the alkali metal ions, which include Na$^+$ or K$^+$, wherein Na$^+$ is most preferred. Further cations X+ may be selected from NH$_4^+$, ½Zn$^{2+}$, ½Mg$^{2+}$, ½Ca$^{2+}$, ½Mn$^{2+}$, and mixtures thereof. Such surfactants may be selected from linear or branched alkyl benzene sulfonates.

Instead of the aforementioned surfactants or in conjunction with them, cationic and/or amphoteric surfactants such as betaines or quaternary ammonium compounds can also be used. It is preferred, however, that no cationic and/or amphoteric surfactants be used.

The builders that can be contained in the dishwashing detergent are in particular silicates, aluminum silicates (in particular zeolites), carbonates, organic di- and polycarboxylic acids and aminocarboxylic acids or the salts thereof, and—where there are no ecological prejudices against the use thereof—also the phosphates. Mixtures of these substances can also be used.

For example, crystalline layered silicates of the general formula NaMSi$_x$O$_{2x+1}$.y H$_2$O can be used, where M represents sodium or hydrogen, x is a number from 1.9 to 22, preferably from 1.9 to 4, wherein 2, 3, or 4 are particularly preferred values for x, and y represents a number from 0 to 33, preferably from 0 to 20. The crystalline layered silicates of the formula NaMSi$_x$O$_{2x+1}$.y H$_2$O are sold, for example, by Clariant GmbH (Germany) under the trade name Na-SKS. Examples of these silicates are Na-SKS-1 (Na$_2$Si$_{22}$O$_{45}$.x H$_2$O, kenyaite), Na-SKS-2 (Na$_2$Si$_{14}$O$_{29}$.x H$_2$O, magadiite), Na-SKS-3 (Na$_2$Si$_{18}$O$_{17}$.x H$_2$O) or Na-SKS-4 (Na$_2$Si$_4$O$_9$.x H$_2$O, macatite). For the purposes of the present invention, crystalline sheet silicates of the formula NaMSi$_x$O$_{2x+1}$.y H$_2$O, in which x is 2, are particularly suitable. In particular, both ß- and δ-sodium disilicates Na$_2$Si$_2$O$_5$.y H$_2$O and, above all, Na-SKS-5 (α-Na$_2$Si$_2$O$_5$), Na-SKS-7 (β-Na$_2$Si$_2$O$_5$, natrosilite), Na-SKS-9 (NaHSi$_2$O$_5$.H$_2$O), Na-SKS-10 (NaHSi$_2$O$_5$.3H$_2$O, kanemite), Na-SKS-11 (t-$Na_2Si_2O_5$) and Na-SKS-13 (NaHSi$_2$O$_5$), but in particular Na-SKS-6 (δ-Na$_2$Si$_2$O$_5$) are preferred. Automatic dishwashing detergents can, if desired, have a weight fraction of the crystalline layered silicate of the formula NaMSi$_x$O$_{2x+1}$·y H$_2$O from 0.1 to 20 wt. % wt. %, preferably 0.2 to 15% wt. % wt. % and in particular 0.4 to 10 wt. %, each based on the total weight of these agents.

Amorphous sodium silicates with an Na$_2$O:SiO$_2$ modulus of from 1:2 to 1:3.3, preferably from 1:2 to 1:2.8 and in particular from 1:2 to 1:2.6, can also be used which preferably have retarded dissolution and secondary washing properties. The retarded dissolution compared to conventional amorphous sodium silicates may have been caused, for example, by way of surface treatment, compounding, compacting/compression or over-drying. Within the scope of this invention, the term "amorphous" is understood to mean that the silicates do not supply any sharp X-ray reflexes in X-ray diffraction experiments, such as those that are typical of crystalline substances, but at best cause one or more maxima of the scattered X-rays, which have a width of several degree units of the diffraction angle.

In the context of the present invention, it is preferred that this/these silicate(s), preferably alkali metal silicates, particularly preferably crystalline or amorphous alkali metal disilicates, are contained in the agents in amounts of 1 to 40 wt. %, preferably from 2 to 35 wt. %, each based on the weight of the automatic dishwashing detergent.

It is self-evidently also possible to use the generally known phosphates as builders, provided that the use thereof should not be avoided for ecological reasons. Among the large number of commercially available phosphates, the alkali metal phosphates, with particular preference for pentasodium or pentapotassium triphosphate (sodium or potassium tripolyphosphate), are of greatest significance in the laundry detergent or dishwashing detergent industry. Alkali metal phosphate is the summary name for the alkali metal (in particular sodium and potassium) salts of the various phosphoric acids, in which metaphosphoric acids (HPO$_3$)$_n$ and orthophosphoric acid H$_3$PO$_4$ can be distinguished in addition to higher molecular weight representatives. The phosphates combine a plurality of advantages: They act as alkali carriers, prevent limescale deposits on machine parts and lime incrustations in fabrics and also contribute to cleaning performance. Technically particularly important phosphates are pentasodium triphosphate, Na$_5$P$_3$O$_{10}$ (sodium tripolyphosphate) and the corresponding potassium salt pentapotassium triphosphate, K$_5$P$_3$O$_{10}$ (potassium tripolyphosphate) and corresponding mixed salts (sodium potassium tripolyphosphates). However, the agents are preferably phosphate-free. If, within the scope of the present application, phosphates are used as active cleaning substances in automatic dishwashing detergents, preferred agents contain this/these phosphate(s), preferably alkali metal phosphate(s), particularly preferably pentasodium or pentapotassium triphosphate (sodium or potassium tripolyphosphate), in amounts of 5 to 80 wt. %, preferably from 10 to 60 wt. % and in particular from 18 to 45 wt. %, based in each case on the weight of the automatic dishwashing detergent.

The dishwashing detergents can in particular also contain phosphonates as a further builder. A hydroxy alkane and/or amino alkane phosphonate is preferably used as a phosphonate compound. Among the hydroxyalkanephosphonates, 1-hydroxyethane-1,1-diphosphonate (HEDP) is of particular importance. Possible preferable aminoalkane phosphonates include ethylenediamine tetramethylene phosphonate (EDTMP), diethylenetriamine pentamethylene phosphonate (DTPMP) and the higher homologs thereof. Phosphonates are preferably contained in the agents in amounts of from 0.1 to 10 wt. %, in particular in amounts of from 0.5 to 8 wt. %, in each case based on the total weight of the dishwashing detergent.

Other builders are the alkali carriers. Alkali carriers include, for example, alkali metal hydroxides, alkali metal carbonates, alkali metal hydrogen carbonates, alkali metal sesquicarbonates, the aforementioned alkali silicates, alkali metasilicates, and mixtures of the aforementioned substances, wherein in the context of this invention the alkali carbonates, in particular sodium carbonate, sodium hydrogen carbonate or sodium sesquicarbonate, can preferably be used. A builder system containing a mixture of tripolyphosphate and sodium carbonate is particularly preferred. A builder system containing a mixture of tripolyphosphate and sodium carbonate and sodium disilicate is also particularly preferred. Due to their low chemical compatibility with the other ingredients of automatic dishwashing detergents compared to other builder substances, the optional alkali metal hydroxides are preferably only used in small amounts, preferably in amounts below 10 wt. %, preferably below 6 wt. %, particularly preferably below 4 wt. % and in particular below 2 wt. %, based in each case on the total weight of the automatic dishwashing detergent. Agents which, based on the total weight thereof, contain less than 0.5 wt. % and in particular no alkali metal hydroxides are particularly preferred. It is particularly preferred to use carbonate(s) and/or hydrogen carbonate(s), preferably alkali carbonate(s), particularly preferably sodium carbonate, in amounts of from 2 to 50 wt. %, preferably from 5 to 40 wt. %, and in particular from 7.5 to 30 wt. %, in each case based on the weight of the automatic dishwashing detergent. Agents which, based on the weight of the automatic dishwashing detergent, contain less than 20 wt. %, preferably less than 17 wt. %, preferably less than 13 wt. % and in particular less than 9 wt. % of carbonate(s) and/or hydrogen carbonate(s), preferably alkali metal carbonate(s), particularly preferably sodium carbonate, are particularly preferred.

Polycarboxylates/polycarboxylic acids, polymeric polycarboxylates, aspartic acid, polyacetals, dextrins, other organic cobuilders and the phosphonates already mentioned above as builders are particularly noteworthy as organic builders. Organic builders that can be used are, for example, the polycarboxylic acids that can be used in the form of the free acids and/or the sodium salts thereof, wherein polycarboxylic acids are understood to mean those carboxylic acids which carry more than one acid function. These include, for example, citric acid, adipic acid, succinic acid, glutaric acid, malic acid, tartaric acid, maleic acid, fumaric acid, saccharic acids, nitrilotriacetic acid (NTA), provided that the use thereof is not objectionable for ecological reasons, and mixtures thereof. In addition to their builder effect, the free acids typically also have the property of being an acidification component and are thus also used for setting a lower and milder pH of the automatic dishwashing detergent. Particularly noteworthy here are citric acid, succinic acid, glutaric acid, adipic acid, gluconic acid, and any mixtures thereof. The use of citric acid and/or citrates has proven to be particularly advantageous for the cleaning and rinsing performance of the agents. Automatic dishwashing detergents which contain citric acid or a salt of citric acid are therefore preferred. Another important class of phosphate-free builders are aminocarboxylic acids and/or the salts thereof. Particularly preferred representatives of this class are methylglycinediacetic acid (MGDA) or the salts thereof, and glutamic diacetic acid (GLDA) or the salts thereof or ethylenediaminediacetic acid or the salts thereof (EDDS).

The concentration of these aminocarboxylic acids or the salts thereof can be, for example, between 0.1 and 30 wt. %, preferably between 1 and 25 wt. % and in particular between 5 and 20 wt. %. Aminocarboxylic acids and the salts thereof can be used together with the aforementioned builders, also with the phosphate-free builders.

The dishwashing detergents may also contain a sulfopolymer. The proportion by weight of the sulfopolymer of the total weight of the dishwashing detergent is preferably from 0.1 to 20 wt. %, in particular from 0.5 to 18 wt. %, particularly preferably from 1.0 to 15 wt. %, in particular from 4 to 14 wt. %, especially from 6 to 12 wt. %. The sulfopolymer is usually used in the form of an aqueous solution, wherein the aqueous solutions typically contain 20 to 70 wt. %, in particular 30 to 50 wt. %, preferably about 35 to 40 wt. %, of sulfopolymers. A copolymeric polysulfonate, preferably a hydrophobically modified copolymeric polysulfonate, is preferably used as sulfopolymer. The copolymers can have two, three, four, or more different monomer units. Preferred copolymeric polysulfonates contain, in addition to sulfonic acid group-containing monomer(s), at least one monomer from the group of unsaturated carboxylic acids. As unsaturated carboxylic acid(s), unsaturated carboxylic acids of formula $R^1(R^2)C=C(R^3)COOH$ are particularly preferably used, in which $R^1$ to $R^3$ represent, independently of one another, —H, —$CH_3$, a straight-chain or branched saturated alkyl radical having 2 to 12 carbon atoms, a straight-chain or branched, mono- or polyunsaturated alkenyl radical having 2 to 12 carbon atoms, —$NH_2$, —OH, or —COOH substituted alkyl or alkenyl radicals as defined above, or represent —COOH or —$COOR^4$, wherein $R^4$ is a saturated or unsaturated, straight-chain or branched hydrocarbon radical having 1 to 12 carbon atoms. Particularly preferred unsaturated carboxylic acids are acrylic acid, methacrylic acid, ethacrylic acid, α-chloroacrylic acid, α-cyanoacrylic acid, crotonic acid, α-phenylacrylic acid, maleic acid, maleic anhydride, fumaric acid, itaconic acid, citraconic acid, methylene malonic acid, sorbic acid, cinnamic acid, or mixtures thereof. Unsaturated dicarboxylic acids can of course also be used. For monomers containing sulfonic acid groups, those of the formula $R^5(R^6)C=C(R^7)$—X—$SO_3H$ are preferred, in which $R^5$ to $R^7$ independently of one another represent —H and —$CH_3$, a straight-chain or branched saturated alkyl radical having 2 to 12 carbon atoms, a straight-chain or branched, mono- or poly-unsaturated alkenyl radical having 2 to 12 carbon atoms, with —$NH_2$-, OH- or —COOH-substituted alkyl or alkenyl radicals, or represent —COOH or —$COOR^4$, wherein $R^4$ is a saturated or unsaturated, straight-chain or branched hydrocarbon radical having 1 to 12 carbon atoms and X represents an optionally present spacer group that is selected from —$(CH_2)_n$, where n=0 to 4, —COO—$(CH_2)_k$—, where k=1 to 6, —C(O)—NH—C$(CH_3)_2$—, —C(O)—NH—C$(CH_3)_2$—$CH_2$— and —C(O)—NH—CH$(CH_3)$ $CH_2$—. Among these monomers, those of formulas $H_2C=CH$—X—$SO_3H$, $H_2C=C(CH_3)$—X—$SO_3H$ and $HO_3S$—X—$(R^6)C=C(R^7)$—X—$SO_3H$ are preferred, in which $R^6$ and $R^7$, independently of one another, are selected from —H, —$CH_3$, —$CH_2CH_3$, —$CH_2CH_2CH_3$ and —CH$(CH_3)_2$, and X represents an optionally present spacer group that is selected from —$(CH_2)_n$—, where n=0 to 4, —COO—$(CH_2)_k$—, where k=1 to 6, C(O)—NH—C$(CH_3)_2$—, C(O)—NH—C$(CH_3)_2$—$CH_2$— and —C(O)—NH—CH$(CH_3)$ $CH_2$—. Particularly preferred sulfonic acid group-containing monomers are 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxy-propanesulfonic acid, allyl sulfonic acid, methallyl sulfonic acid, allyloxybenzene sulfonic acid, methallyloxybenzene sulfonic acid, 2-hydroxy-3-(2-propenyloxy)propanesulfonic acid, 2-methyl-2-propene-1-sulfonic acid, styrene sulfonic acid, vinylsulfonic acid, 3-sulfopropyl acrylate, 3-sulfopropyl methacrylate, sulfomethacrylamide, sulfomethylmethacrylamide, and mixtures of the above acids or the water-soluble salts thereof. The sulfonic acid groups can be present in the polymers in a fully or partially neutralized form, i.e. the acidic hydrogen atom of the sulfonic acid group can be replaced in some or all of the sulfonic acid groups with metal ions, preferably alkali metal ions, and in particular with sodium ions. The use of partially or fully neutralized copolymers containing sulfonic acid groups is preferred according to the invention. In copolymers that contain only monomers containing carboxylic acid groups and monomers containing sulfonic acid groups, the monomer distribution of the copolymers that are preferably used is preferably 5 to 95 wt. % in each case; particularly preferably, the proportion of the sulfonic acid group-containing monomers is 50 to 90 wt. %, and the proportion of the carboxylic acid group-containing monomers is 10 to 50 wt. %, with the monomers preferably being selected from those mentioned above. The molar mass of the sulfo-copolymers that are preferably used can be varied in order to adapt the properties of the polymers to the desired intended use. Preferred dishwashing detergents are characterized in that the copolymers have molar masses from 2000 g/mol to 200,000 g/mol, preferably from 4000 g/mol to 25,000 g/mol and in particular from 5000 g/mol to 15,000 g/mol.

The dishwashing detergents may also contain other polymers. The group of suitable polymers includes, in particular, the active cleaning polymers, for example the rinse aid polymers and/or polymers effective as softeners. Preferred polymers that can be used come from the group of the alkyl acrylamide/acrylic acid copolymers, the alkyl acrylamide/methacrylic acid copolymers, the alkyl acrylamide/methyl methacrylic acid copolymers, the alkyl acrylamide/acrylic acid/alkylaminoalkyl (meth) acrylic acid copolymers, the alkyl acrylamide/methacrylic acid/alkylaminoalkyl (meth) acrylic acid copolymers, the alkyl acrylamide/methyl methacrylic acid/alkylaminoalkyl (meth) acrylic acid copolymers, the alkyl acrylamide/alkymethacrylate/alkylaminoethyl methacrylate/alkyl methacrylate copolymers and the copolymers of unsaturated carboxylic acids, cationically derivatized unsaturated carboxylic acids and, where appropriate, other ionic or nonionogenic monomers. Other polymers that can be used come from the group of acrylamido-alkyltrialkylammonium chloride/acrylic acid copolymers and the alkali and ammonium salts thereof, the acrylamido-alkyltrialkylammonium chloride/methacrylic acid copolymers and the alkali and ammonium salts thereof, and methacroylethylbetaine/methacrylate copolymers. Cationic polymers which can be used originate from the groups of the quaternized cellulose derivatives, the polysiloxanes with quaternary groups, the cationic guar derivatives, the polymeric dimethyldiallylammonium salts and the copolymers thereof with acrylic acid and methacrylic acid and the esters and amides thereof, the copolymers of vinylpyrrolidone with quaternylated derivatives of dialkylamino-acrylate and methacrylate, the vinylpyrrolidone-methoimidazolinium chloride copolymers, the quaternized polyvinyl alcohols or the polymers specified under the INCI names Polyquaternium 2, Polyquaternium 17, Polyquaternium 18 and Polyquaternium 27.

The agents of the present invention preferably contain at least one enzyme preparation or enzyme composition which contains one or more enzymes. Suitable enzymes include, without being limited thereto, proteases, amylases, lipases, hemicellulases, cellulases, perhydrolases or oxidoreductases, and preferably mixtures thereof. Said enzymes are in principle of natural origin; proceeding from the natural molecules, improved variants for use in dishwashing detergents are available which are preferably used accordingly. The agents preferably contain enzymes in total amounts of from $1 \times 10^{-6}$ to 5 wt. %, based on active protein. The protein concentration can be determined using known methods, for example the BCA method or the Biuret method.

Proteases are some of the technically most important enzymes. They bring about the decomposition of protein-containing stains on the item to be cleaned. Of these, in turn, proteases of the subtilisin type (subtilases, subtilopeptidases, EC 3.4.21.62) are particularly important and are serine proteases due to the catalytically active amino acids. They act as non-specific endopeptidases and hydrolyze any acid amide bonds that are inside peptides or proteins. Their optimum pH is usually in the distinctly alkaline range. Subtilases are, naturally, formed from microorganisms. In particular, the subtilisins formed and secreted by *Bacillus* species are the most significant group of subtilases. Examples of the subtilisin proteases preferably used in laundry detergents and dishwashing detergents are the subtilisins BPN' and Carlsberg, the protease PB92, the subtilisins 147 and 309, the protease from *Bacillus lentus*, in particular from *Bacillus lentus* DSM 5483, subtilisin DY and the enzymes thermitase, proteinase K and the proteases TW3 and TW7, which can be classified as subtilases but no longer as subtilisins in the narrower sense, and variants of said proteases which have an amino acid sequence that has been altered with respect to the starting protease. Proteases are altered, selectively or randomly, by methods known from the prior art, and are thereby optimized for use in laundry detergents and dishwashing detergents, for example. These methods include point, deletion or insertion mutagenesis, or fusion with other proteins or protein parts. Appropriately optimized variants are therefore known for the majority of proteases known from the prior art.

Examples of amylases that can be used are the α-amylases from *Bacillus licheniformis*, from *B. amyloliquefaciens*, from *B. stearothermophilus*, from *Aspergillus niger*, and *A. oryzae*, as well as the further developments of said amylases that have been improved for use in dishwashing detergents. Others that are particularly noteworthy for this purpose are the α-amylases from *Bacillus* sp. A 7-7 (DSM 12368) and cyclodextrin glucanotransferase (CGTase) from *B. agaradherens* (DSM 9948).

Furthermore, lipases or cutinases can be used, in particular due to the triglyceride-cleaving activities thereof, but also in order to produce peracids in situ from suitable precursors. These include, for example, the lipases that can originally be obtained from *Humicola lanuginosa* (*Thermomyces lanuginosus*) or those that have been developed therefrom, in particular those having the amino acid exchange D96L.

Moreover, enzymes can be used which can be grouped together under the term "hemicellulases." These include, for example, mannanases, xanthan lyases, pectin lyases (=pectinases), pectinesterases, pectate lyases, xyloglucanases (=xylases), pullulanases, and β-glucanases.

In order to increase the bleaching effect, oxidoreductases such as oxidases, oxygenases, catalases, peroxidases such as halo-, chloro-, bromo-, lignin, glucose, or manganese peroxidases, dioxygenases or laccases (phenoloxidases, polyphenoloxidases) can be used. Advantageously, organic, particularly preferably aromatic compounds that interact with the enzymes are additionally added in order to enhance the activity of the relevant oxidoreductases (enhancers) or, in the event of greatly differing redox potentials, to ensure the flow of electrons between the oxidizing enzymes and the stains (mediators).

An enzyme can be protected, particularly during storage, against damage such as inactivation, denaturing, or decomposition caused, for example, by physical influences, oxidation or proteolytic cleavage. When the proteins and/or enzymes are obtained microbially, it is particularly preferable for proteolysis to be inhibited, in particular if the agents also contain proteases. Dishwashing detergents may contain stabilizers for this purpose; the provision of such agents constitutes a preferred embodiment of the present invention.

Active cleaning enzymes are generally not provided in the form of pure protein, but rather in the form of stabilized, storable and transportable preparations. These pre-formulated preparations include, for example, the solid preparations obtained through granulation, extrusion, or lyophilization or, in particular in the case of liquid or gel agents, solutions of the enzymes, advantageously maximally concentrated, low-water, and/or supplemented with stabilizers or other auxiliaries.

Alternatively, the enzymes can also be encapsulated, for both the solid and the liquid administration form, for example by spray-drying or extrusion of the enzyme solution together with a preferably natural polymer or in the form of capsules, for example those in which the enzymes are enclosed in a set gel, or in those of the core-shell type, in which an enzyme-containing core is coated with a water-, air-, and/or chemical-impermeable protective layer. Further active ingredients such as stabilizers, emulsifiers, pigments, bleaching agents, or dyes can additionally be applied in overlaid layers. Such capsules are applied using inherently known methods, for example by shaking or roll granulation or in fluidized bed processes. Such granules are advantageously low in dust, for example due to the application of polymeric film-formers, and stable in storage due to the coating.

Moreover, it is possible to formulate two or more enzymes together such that a single granule exhibits a plurality of enzyme activities.

As a rule, the enzyme protein forms only a fraction of the total weight of conventional enzyme preparations. Enzyme preparations that are preferably used contain between 0.1 and 40 wt %, preferably between 0.2 and 30 wt %, particularly preferably between 0.4 and 20 wt %, and in particular between 0.8 and 10 wt % of the enzyme protein.

In particular, those dishwashing detergents are preferred which contain, based on their total weight, 0.1 to 12 wt. %, preferably 0.2 to 10 wt. %, and in particular 0.5 to 8 wt. % enzyme preparations.

The compositions described herein may also include enzyme stabilizers. One group of stabilizers are reversible protease inhibitors. Benzamidine hydrochloride, borax, boric acids, boronic acids or the salts or esters thereof are frequently used for this purpose, including above all derivatives having aromatic groups, for example ortho-, meta- or para-substituted phenylboronic acids, in particular 4-formylphenylboronic acid, or the salts or esters of the aforementioned compounds. Peptide aldehydes, i.e. oligopeptides having a reduced C-terminus, in particular those consisting of 2 to 50 monomers, are also used for this purpose. The peptide reversible protease inhibitors include, inter alia, ovomucoid and leupeptin. Specific, reversible peptide inhibitors for the protease subtilisin and fusion proteins from proteases and specific peptide inhibitors are also suitable for this purpose. Other enzyme stabilizers are amino alcohols such as mono-, di-, triethanol- and -propanolamine and mixtures thereof, aliphatic carboxylic acids up to $C_{12}$, such as succinic acid, other dicarboxylic acids or salts of the aforementioned acids. End-capped fatty acid amide alkoxylates are also suitable for this purpose. Further enzyme stabilizers are known from the prior art to a person skilled in the art.

Bleaching agents are active cleaning substances. From the group of compounds which act as bleaching agents and yield $H_2O_2$ in water, sodium percarbonate, sodium perborate tetrahydrate and sodium perborate monohydrate are of particular significance. Further examples of bleaching agents which may be used are peroxypyrophosphates, citrate perhydrates as well as $H_2O_2$-yielding peracid salts or peracids, such as perbenzoates, peroxophthalates, diperazelaic acid, phthaloiminoperacid or diperdodecane diacid. All other inorganic or organic peroxy bleaches known from the prior art to a person skilled in the art can also be used. The percarbonates, and here in particular sodium percarbonate, are particularly preferred as bleaching agents. The dishwashing detergents, in various embodiments, can contain 1 wt. % to 35 wt. %, preferably 2.5 wt. % to 30 wt. %, particularly preferably 3.5 wt. % to 20 wt. % and in particular 5 wt. % to 15 wt. % bleach, preferably sodium percarbonate.

In various embodiments of the invention, the automatic dishwashing detergents additionally contain at least one bleach activator. Compounds which, under perhydrolysis conditions, result in aliphatic peroxocarboxylic acids having preferably 1 to 10 C atoms, in particular 2 to 4 C atoms, and/or optionally substituted perbenzoic acid, may be used as bleach activators. Of all the bleach activators known from the prior art to a person skilled in the art, a plurality of acylated alkylenediamines, in particular tetraacetylethylenediamine (TAED), acylated triazine derivatives, in particular 1,5-diacetyl-2,4-dioxohexahydro-1,3,5-triazine (DADHT), are acylated glycolurils, in particular tetraacetylglycoluril (TAGU), N-acylimides, in particular N-nonanoylsuccinimide (NOSI), acylated phenol sulfonates, in particular n-nonanoyl or isononanoyloxybenzenesulfonate (n- or iso-NOBS) are particularly preferred. Combinations of conventional bleach activators can also be used. TAED, in particular in combination with a percarbonate bleach, preferably sodium percarbonate, is very particularly preferred as the bleach activator. These bleach activators are preferably used in amounts of up to 10 wt. %, in particular 0.1 wt. % to 8 wt. %, especially 2 wt. % to 8 wt. % and particularly preferably 2 wt. % to 6 wt. %, based in each case on the total weight of the agent.

In general, the pH of the dishwashing detergent can be adjusted by means of customary pH regulators, wherein the pH is selected depending on the intended use. In various embodiments, the pH is in a range from 5.5 to 10.5, preferably 5.5 to 9.5, even more preferably 7 to 9, in particular greater than 7, especially in the range 7.5 to 8.5. Acids and/or alkalis, preferably alkalis, are used as pH adjusting agents. Suitable acids are, in particular, organic acids, such as acetic acid, citric acid, glycolic acid, lactic acid, succinic acid, adipic acid, malic acid, tartaric acid and gluconic acid, or sulfamic acid. In addition, however, the mineral acids hydrochloric acid, sulfuric acid and nitric acid or mixtures thereof can also be used. Suitable bases originate from the group of alkali and alkaline-earth metal hydroxides and carbonates, in particular alkali metal hydroxides, of which potassium hydroxide and especially sodium hydroxide is preferred. However, volatile alkali is particularly preferred, for example in the form of ammonia and/or alkanolamines, which can contain up to 9 carbon atoms in the molecule. The alkanolamine is preferably selected from the group consisting of mono-, di-, triethanol- and propanolamine and mixtures thereof. To adjust and/or stabilize the pH, the agent according to the invention can also contain one or more buffer substances (INCI buffering agents), usually in amounts from 0.001 to 5 wt. %. Buffer substances, which are also complexing agents or even chelating agents (chelators, INCI chelating agents), are preferred. Particularly preferred buffer substances are citric acid and the citrates, in particular the sodium and potassium citrates, for example trisodium citrate, $2H_2O$ and tripotassium citrate $H_2O$.

Glass corrosion inhibitors prevent the appearance of cloudiness, streaks and scratches, but also the iridescence of the glass surface of dishwasher-cleaned glasses. Preferred glass corrosion inhibitors come from the group of the magnesium and zinc salts and the magnesium and zinc complexes. In the context of the present invention, the concentration of zinc salt in dishwashing detergents is preferably in the range from 0.1 wt. % to 5 wt. %, preferably from 0.2 wt. % to 4 wt. % and in particular from 0.4 wt. % to 3 wt. %, each based on the total weight of the glass corrosion inhibitor-containing agent.

Individual odorant compounds, for example the synthetic products of the ester, ether, aldehyde, ketone, alcohol, and hydrocarbon types, can be used as perfume oils or fragrances in the context of the present invention. However, mixtures of different odorants are preferably used which together produce an appealing fragrance note. Perfume oils of this kind can also contain natural odorant mixtures, as are obtainable from plant sources, for example, pine, citrus, jasmine, patchouli, rose or ylang-ylang oil.

Preservatives may also be contained in the agents. For example, preservatives from the groups of the alcohols, aldehydes, antimicrobial acids and/or the salts thereof, carboxylic acid esters, acid amides, phenols, phenol derivatives, diphenyls, diphenyl alkanes, urea derivatives, oxygen and nitrogen acetals and methylals, benzamidines, isothiazoles and the derivatives thereof, such as isothiazolins and isothiazolinones, phthalimide derivatives, pyridine derivatives, antimicrobial surface-active compounds, guanidines, antimicrobial amphoteric compounds, quinolines, 1,2-dibromo-2,4-dicyanobutane, iodo-2-propynyl-butyl-carbamate, iodine, iodophors, and peroxides are suitable. Preferred antimicrobial active ingredients are preferably selected from the group comprising ethanol, n-propanol, i-propanol, 1,3-butanediol, phenoxyethanol, 1,2-propylene glycol, glycerol, undecylenic acid, citric acid, lactic acid, benzoic acid, salicylic acid, thymol, 2-benzyl-4-chlorophenol, 2,2'-methylene-bis-(6-bromo-4-chlorophenol), 2,4,4'-trichloro-2'-hydroxydiphenyl ether, N-(4-chlorophenyl)-N'-(3,4-dichlorophenyl)-urea, N,N'-(1,10-decandiyldi-1-pyridinyl-4-ylidene)-bis-(1-octanamine)-dichloride, N,N'-bis-(4-chlorophenyl)-3,12-diimino-2,4,11,13-tetraazatetradecandiimidamide, antimicrobial quaternary surface-active compounds, guanidines. Particularly preferred preservatives are, however, selected from the group comprising salicylic acid, quaternary surfactants, in particular benzalkonium chloride and isothiazoles and the derivatives thereof such as isothiazolines and isothiazolinones.

In general, the automatic dishwashing detergents described herein can be packaged in different ways. The agents can be in solid or liquid form, as well as a combination of solid and liquid forms. Powder, granules, extrudates or compacted products, in particular tablets, are particularly suitable as solid product formats. The water- and/or organic-solvent-based liquid product formats may be present in thickened form, namely in the form of gels. The agents may be prepared in the form of single-phase or multi-phase products. The individual phases of multiphase agents can have the same or different states of matter.

The dishwashing detergents can be in the form of shaped bodies. In order to facilitate the disintegration of such prefabricated shaped bodies, it is possible to incorporate disintegration aids, so-called tablet disintegrants, into these agents in order to shorten the disintegration times. Tablet disintegrants or disintegration accelerators are understood as meaning auxiliaries which ensure the rapid disintegration of tablets in water or other media and the rapid release of the active ingredients. Disintegration aids can preferably be used in amounts of 0.5 to 10 wt. %, preferably 3 to 7 wt. % and in particular 4 to 6 wt. %, based in each case on the total weight of the agent containing the disintegration aid.

The automatic dishwashing detergents described herein are preferably pre-packaged into metering units. These metering units preferably comprise the amount of active cleaning substances necessary for a cleaning cycle. Preferred metering units have a weight between 12 and 30 g, preferably between 14 and 26 g and in particular between 16 and 22 g. The volume of the aforementioned metering units and the spatial shape thereof are particularly preferably selected so that the pre-packaged units can be metered via the metering chamber of a dishwasher. The volume of the metering unit is therefore preferably between 10 and 35 ml, preferably between 12 and 30 ml.

The automatic dishwashing detergents, in particular the prefabricated metering units, particularly preferably have a water-soluble coating. The water-soluble wrapping is preferably made from a water-soluble film material, which is selected from the group consisting of polymers or polymer mixtures. The wrapping may be made up of one or of two or more layers of the water-soluble film material. The water-soluble film material of the first layer and of the additional layers, if present, may be the same or different. Particularly preferred are foils which, for example, can be glued and/or sealed to form packaging such as tubes or sachets after they have been filled with an agent.

The water-soluble packaging may have one or more chambers. The agent may be contained in one or more chambers, if present, of the water-soluble wrapping. The amount of agent preferably corresponds to the full or half dose required for a dishwashing cycle.

It is preferable for the water-soluble wrapping to contain polyvinyl alcohol or a polyvinyl alcohol copolymer. Water-soluble wrappings containing polyvinyl alcohol or a polyvinyl alcohol copolymer exhibit good stability with a sufficiently high level of water solubility, in particular cold-water solubility. Suitable water-soluble films for producing the water-soluble wrapping are preferably based on a polyvinyl alcohol or a polyvinyl alcohol copolymer of which the molecular weight is in the range of from 10,000 to 1,000,000 g/mol, preferably from 20,000 to 500,000 g/mol, particularly preferably from 30,000 to 100,000 g/mol, and in particular from 40,000 to 80,000 g/mol. Polyvinyl alcohol is usually prepared by hydrolysis of polyvinyl acetate since the direct synthesis route is not possible. The same applies to polyvinyl alcohol copolymers, which are prepared accordingly from polyvinyl acetate copolymers. It is preferable for at least one layer of the water-soluble wrapping to include a polyvinyl alcohol of which the degree of hydrolysis is 70 mol. % to 100 mol. %, preferably 80 mol. % to 90 mol. %, particularly preferably 81 mol. % to 89 mol. %, and in particular 82 mol. % to 88 mol. %. In addition, a polymer selected from the group including (meth)acrylic acid-containing (co)polymers, polyacrylamides, oxazoline polymers, polystyrene sulfonates, polyurethanes, polyesters, polyethers, polylactic acid or mixtures of said polymers may be added to a polyvinyl alcohol-containing film material that is suitable for producing the water-soluble wrapping. Polylactic acids are a preferred additional polymer. Preferred polyvinyl alcohol copolymers include, in addition to vinyl alcohol, dicarboxylic acids as further monomers. Suitable dicarboxylic acids are itaconic acid, malonic acid, succinic acid and mixtures thereof, wherein itaconic acid is preferred. Polyvinyl alcohol copolymers which include, in addition to vinyl alcohol, an ethylenically unsaturated carboxylic acid or the salt or ester thereof, are also preferred. Polyvinyl alcohol copolymers of this kind particularly preferably contain, in addition to vinyl alcohol, acrylic acid, methacrylic acid, acrylic acid ester, methacrylic acid ester or mixtures thereof. It may be preferable for the film material to contain further additives. The film material may contain plasticizers such as dipropylene glycol, ethylene glycol, diethylene glycol, propylene glycol, glycerin, sorbitol, mannitol or mixtures thereof, for example. Further additives include for example release aids, fillers, cross-linking agents, surfactants, antioxidants, UV absorbers, anti-blocking agents, anti-adhesive agents or mixtures thereof. Suitable water-soluble films for use in the water-soluble wrappings of the water-soluble packaging according to the invention are films which are sold by MonoSol LLC, for example under the names M8630, C8400 or M8900. Other suitable films include films named Solublon® PT, Solublon® GA, Solublon® KC or Solublon® KL from Aicello Chemical Europe GmbH, or the VF-HP films from Kuraray.

In the automatic dishwashing method according to the invention, the agent according to the invention is metered into the interior of a dishwasher while a dishwasher program is running before the start of the main wash cycle or during the main wash cycle. The metering or introduction of the agent according to the invention into the interior of the dishwasher can take place manually, but the agent is preferably metered into the interior of the dishwasher by means of the metering chamber.

EXAMPLES

Example 1: Ligand Production

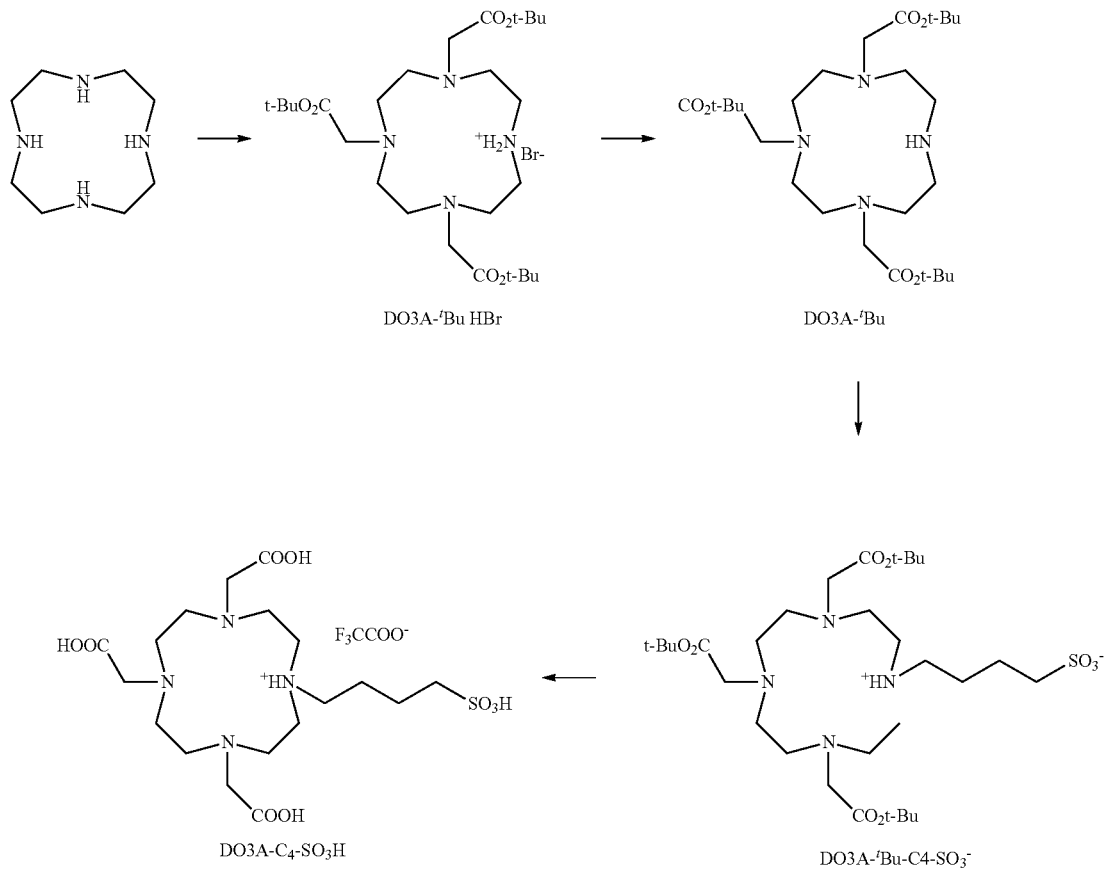

The first two steps are published by B. Jagadish et al. in Tetrahedron Letters 52 (2011) 2058-2061.

A solution of 18.7 g of bromoacetic acid tert-butyl ester (96 mmol) in 20 ml of N, N-dimethylacetamide was added dropwise at −20° C. within 30 minutes to a vigorously stirred mixture of 5.00 g of tetraazacyclodecane (29 mmol) and 7.87 g of sodium acetate in 60 ml of N,N-dimethylacetamide. The reaction mixture was then stirred at room temperature for 24 hours, then added to 300 ml of distilled water, and 15 g of $KHCO_3$ were added. The forming precipitate was filtered off and dissolved in 250 ml of chloroform. After washing with 100 ml of water and drying with magnesium sulfate, the solution was concentrated to a volume of about 25 ml, 250 ml of diethyl ether were added and the forming precipitate was filtered off, washed twice with diethyl ether and dried under vacuum. 12.37 g (71%) DO3A-$^t$Bu HBr were obtained which was characterized by means of $^1$H-NMR spectroscopy in $CDCl_3$ and ESI-MS.

9.4 ml of a 10 percent strength by weight aqueous KOH solution were added at 40° C. to a solution of 5.00 g of the hydrobromide thus obtained (8.4 mmol) in 250 ml of distilled water, and the reaction mixture was stirred for 30 minutes and then extracted 3 times with 100 ml of hexane each time. The combined organic phases were washed 3 times with 100 ml of distilled water each time and dried with magnesium sulfate. Removal of the solvent under reduced pressure gave a colorless oil which solidified on cooling to −20° C. 3.80 g (88%) DO3A-$^t$Bu, which was characterized by means of $^1$H-NMR spectroscopy in $CDCl_3$ and ESI-MS, were obtained.

A solution of 0.45 g of freshly distilled 1,4-butane sultone (3.3 mmol) was added within 20 minutes under an $N_2$ atmosphere to a solution, heated to boiling under reflux, of 1.60 g of the free base (3.1 mmol) obtained in this way in 20 ml of anhydrous tetrahydrofuran. After heating to boiling under reflux for 48 hours, the solvent was removed under vacuum and the residue was absorbed into methanol/diethyl ether (volumetric ratio 1:30), heated to 40° C. and then kept at −20° C. overnight. The precipitated sediment was filtered off using a glass frit, washed 3 times with 20 ml of diethyl ether each time and dried under vacuum. 1.53 g (76%) of DO3A-$^t$Bu-C4-$SO_3^-$, which was characterized by means of $^1$H-, $^{13}$C-, $^{15}$N-NMR and ATR-IR spectroscopy and ESI-MS, were obtained.

1.53 g of the zwitterionic ester obtained in this way were stirred vigorously under an $N_2$ atmosphere in 20 ml of trifluoroacetic acid at 25° C. for 24 hours. Trifluoroacetic acid was then removed under vacuum, the colorless residue was absorbed into 2 ml of methanol, and 50 ml of diethyl ether were added at 5° C. After stirring for 2 hours at 25° C., the deposited precipitate was filtered off using a glass frit and dried under vacuum. The DO3A-$^t$Bu-C4-$SO_3$H trifluoroacetate, which was characterized by means of $^1$H-, $^{13}$C-NMR and ATR-IR spectroscopy and ESI-MS, was obtained in quantitative yield.

Example 2: Further Ligand Production

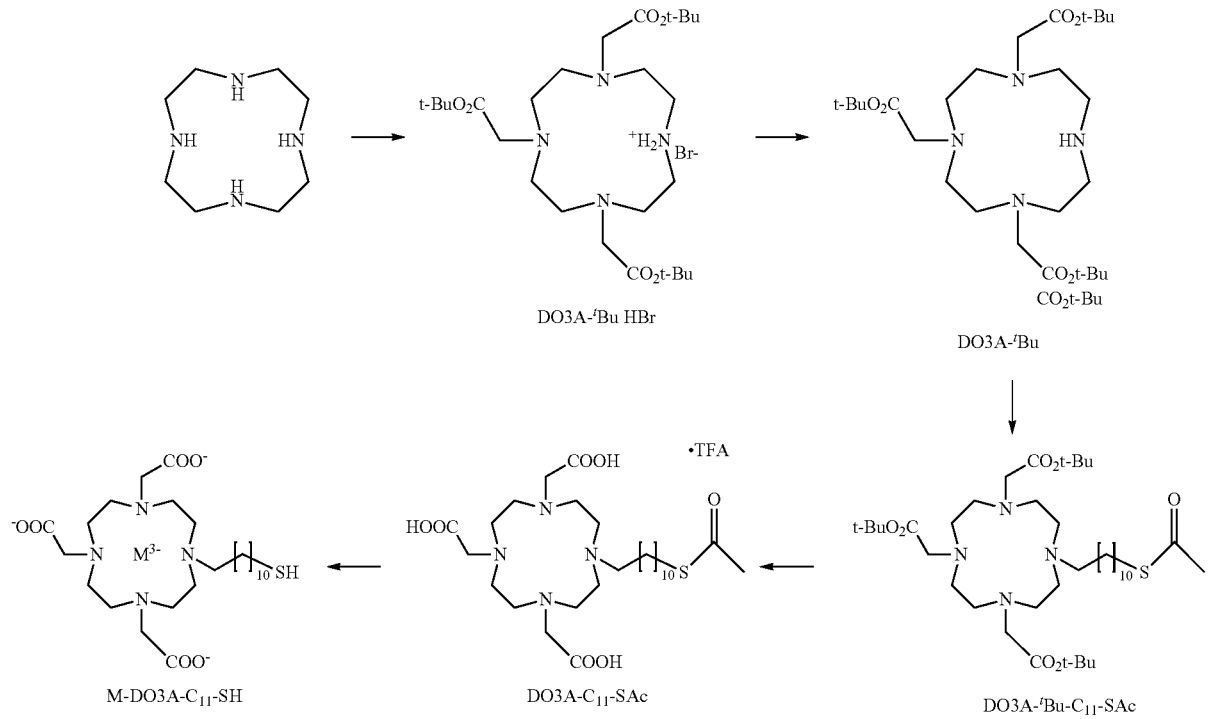

A solution of 0.33 g of S-(11-bromundeceyl)-thioacetate (1.07 mmol) in 10 ml of $CHCl_3$ was added dropwise to a solution of 0.5 g of the free base DO3A-$^t$Bu (1 mmol) produced as intermediate product in Example 1 and heated to boiling under reflux and 0.12 g of triethylamine (1.2 mmol) in 20 ml of anhydrous $CHCl_3$ under an $N_2$ atmosphere. After being heated to boiling under reflux for 24 hours, the reaction mixture was cooled to room temperature and washed with 20 ml of distilled water. After drying with $MgSO_4$, the solvent was removed under vacuum. DO3A-$^t$Bu-C11-SAc was obtained in quantitative yield as a pale yellow solid.

$^1$H-NMR (400 MHz, $CDCl_3$): δ 1.23-1.37 (br m, 18H), 1.43-1.47 (br s, 27H), 2.31 (s, 3H), 2.50-3.23 (br m, 18H), 3.26-3.46 (br m, 8H).

ESI-MS (+): 743,530 ([M+H]$^+$, calculated 743,535).

A solution of 0.63 g of the ester obtained in this way in 10 ml of $CH_2Cl_2$ was mixed with 20 ml of trifluoroacetic acid under an $N_2$ atmosphere and stirred at 25° C. for 48 hours. The solvents were then removed under reduced pressure, the yellow oily residue was absorbed into 2 ml of methanol, and 50 ml of diethyl ether were added at 5° C. After stirring for 4 hours at 25° C., the precipitate which had separated out was isolated by decanting, washing several times with diethyl ether and drying under vacuum. The DO3A-C11-SAc trifluoroacetate was obtained in an 82% yield.

$^1$H-NMR (400 MHz, $D_2O$): δ 1.25-1.45 (br m, 14H), 1.52-1.66 (q, 2H), 1.68-1.85 (m, 2H), 2.35-2.43 (s, 3H), 2.87-2.95 (t, 2H), 3.03-3.31 (m, 12H), 3.39-3.67 (m, 10H), 3.91 (s, 2H).

ESI-MS (+): 575,380 ([M+H]$^+$, calculated 575,347).

To remove the acetate protective group, a solution of 0.34 g of the trifluoroacetic acid adduct obtained in this way was stirred into 10 ml of 7 M $NH_3$ in anhydrous $CH_3OH$ for 15 minutes under an $N_2$ atmosphere.

Example 3: Synthesis of Metal Complexes

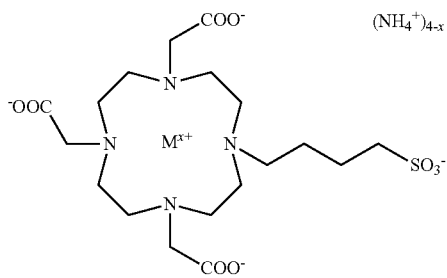

with $M^{x+}$=$Ce^{3+}$, $Zn^{2+}$, $Yb^{3+}$, $Sc^{3+}$

Solutions of 246 mg $CeCl_3$, 136 mg $ZnCl_2$, 279 mg $YbCl_3$ or 151 mg $ScCl_3$ in 5 ml of dry methanol were added dropwise to solutions of 597 mg of the trifluoroacetate obtained in Example 1 in 10 ml of 7 M $NH_3$ in anhydrous methanol under an $N_2$ atmosphere. The reaction mixtures were heated to boiling under reflux for 48 hours, then cooled to room temperature, and the solvent was removed under vacuum. The residue was absorbed in 20 ml of double-distilled water, treated with ultrasound for 5 minutes, and undissolved material was filtered off. After removal of the solvent, the Ce, Zn, Yb and Sc complexes were obtained in quantitative yield as colorless solids.

Example 4: Synthesis of Another Metal Complex

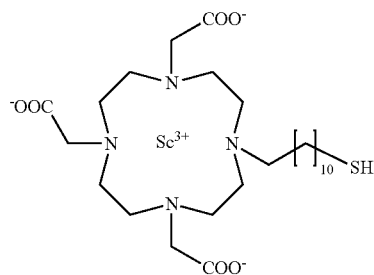

A solution of 78 mg of anhydrous $ScCl_3$ (0.52 mmol) in 5 ml of dry methanol was added dropwise to the solution prepared in Example 2 under an $N_2$ atmosphere. The reaction mixture was heated to 75° C. for 72 hours and, after removal of undissolved residues with the aid of a syringe filter, the solvent was removed under vacuum. The solid residue was recrystallized from $CH_3OH$/diethyl ether (1:50); after drying, 0.29 g of the Sc complex was obtained as a colorless solid, which was characterized by ESI-MS.

$^1$H-NMR (600 MHz, MeOH-d4): δ 1.20-1.70 (m, 18H), 2.42-3.26 (m, 18H), 3.38-4.00 (m, 8H).

$^{13}$C-NMR (125 MHz, MeOH-d4): δ 18.9, 19.0, 22.8, 26.6, 26.9, 27.2, 28.0, 28.5, 28.6, 50.6, 53.5, 54.2, 55.3, 64.6, 65.1, 65.3, 65.6, 65.9, 66.2, 174.2, 177.6.

Example 5: Hydrolysis of Protein Soiling

The hydrolysis of protein soil was investigated using the breakdown of ovalbumin (hen's egg albumin, about 45 kDa). For this purpose, an aqueous ovalbumin solution (concentration of ovalbumin 0.02 mM) was mixed with a complex indicated below (concentration of the complex 1 mM), so that the concentration of ovalbumin was 0.02 mM and the concentration of the complex was 1 mM, incubated at 60° C. and pH 6 (adjusted with NaOH and HCl) for 1 hour, 5 hours or 24 hours. The incubated material was then examined with the known method of SDS-PAGE with regard to the intensity of the band to be assigned to ovalbumin. Ovalbumin incubated under the same conditions without the addition of complexes served as reference. The intensity values given in Table 1 below are relative values based on the intensity of the reference band at t=0. The smaller the value after the incubation, the greater the degradation of the protein soiling.

The complexes Ce-DO3A-C4-SO3$^-$ (K1), Yb-DO3A-C4-SO3$^-$ (K2), Sc-DO3A-C4-SO3$^-$ (K3) produced in example 3 and for comparison the complex known from WO 2016/062784 A1

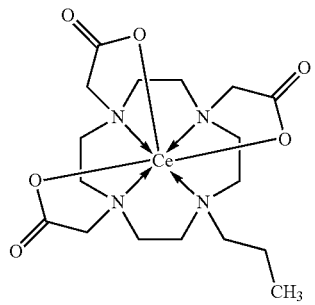

(V1) were tested.

TABLE 1

| Complex | Intensity at t = 1 h | Intensity at t = 5 h | Intensity at t = 24 h |
| --- | --- | --- | --- |
| — | 0.97 | 0.97 | 1.05 |
| V1 | 0.96 | 0.95 | 0.82 |
| K1 | 0.86 | 0.76 | 0.70 |
| K2 | 0.79 | 0.69 | 0.50 |
| K3 | 0.78 | 0.66 | 0.59 |

It can be seen that the complexes essential to the invention break down the protein soiling significantly more than the known complex with the alkyl substituent on the nitrogen atom.

BSA was completely degraded by the complex prepared in Example 4 (complex concentration 2 mM) and an incubation time of 16 hours under otherwise identical conditions.

What is claimed is:

1. A compound of the general formula (I),

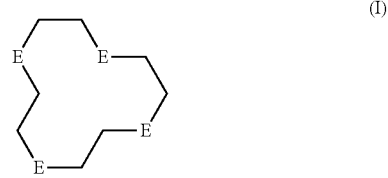

in which each E independently represents O or $NR^1$, with the proviso that at least 1 E is not O, each $R^1$ independently represents H, unsubstituted or substituted, linear or branched $C_{1-22}$ alkyl, unsubstituted or substituted, linear or branched $C_{1-22}$ heteroalkyl, unsubstituted or substituted aryl, unsubstituted or substituted heteroaryl, unsubstituted or substituted, linear or branched $C_{2-20}$ alkenyl, unsubstituted or substituted, linear or branched $C_{2-20}$ alkynyl, unsubstituted or substituted, linear or branched $C_{2-20}$ heteroalkenyl, unsubstituted or substituted, linear or branched alkylaryl, or unsubstituted or substituted, linear or branched alkylheteroaryl, with the proviso that at least 1 $R^1$ represents a substituted $C_{1-22}$ alkyl of the general formula (IIa) or (IIb), or with the proviso that at least 1 $R^1$ is a substituted $C_{1-22}$ alkyl of the general formula (IIIa) or (IIIb),

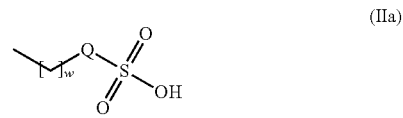

(IIa)

(IIb)

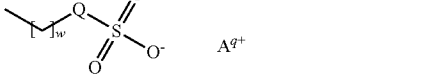

(IIIa)

(IIIb)

in which Q represents O or $CH_2$, w represents a number from 1 to 22, q represents 1 or 2 and $A^+$ represents a cation selected from alkali metal cations where q=1, ½ alkaline earth cations where q=2 and ammonium ions where q=1;

wherein in the general formula (I) the groups R¹ which do not correspond to the general formula (IIa), or (IIb) are selected from the group consisting of

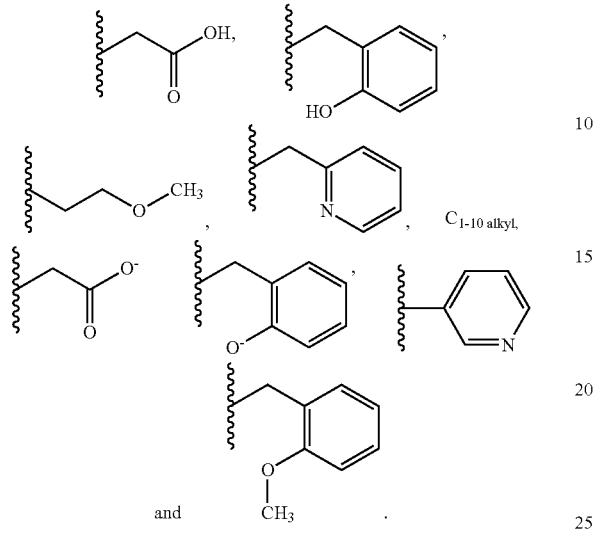

and

2. The compound according to claim 1 wherein, in the general formula (I), w represents a number from 2 to 20.

3. The compound according to claim 1 wherein, w represents a number from 3 to 18.

4. A dishwashing detergent comprising a metal complex of the general formula (III), $$(A^{q+})_p[M^{n+}L^{m-}](X^{o-}),\quad\text{(III)}$$

in which q represents 1 or 2 and A⁺ represents a cation selected from alkali metal cations where q=1, ½ alkaline earth cations where q=2 and ammonium ions where q=1, M$^{n+}$ represents an aluminum ion, a transition metal ion or a lanthanoid metal ion, L represents a ligand of the formula (I)

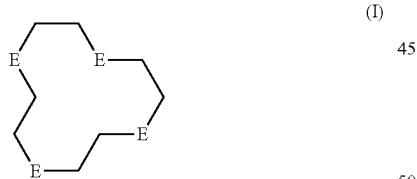

in which each E independently represents O or NR¹, with the proviso that at least 1 E is not O, each R¹ independently represents H, unsubstituted or substituted, linear or branched C$_{1-22}$ alkyl, unsubstituted or substituted, linear or branched C$_{1-22}$ heteroalkyl, unsubstituted or substituted aryl, unsubstituted or substituted heteroaryl, unsubstituted or substituted, linear or branched C$_{2-20}$ alkenyl, unsubstituted or substituted, linear or branched C$_{2-20}$ alkynyl, unsubstituted or substituted, linear or branched C$_{2-20}$ heteroalkenyl, unsubstituted or substituted, linear or branched alkylaryl, or unsubstituted or substituted, linear or branched alkylheteroaryl, with the proviso that at least 1 R¹ represents a substituted C$_1$-22 alkyl of the general formula (IIa) or (IIc), or with the proviso that at least 1 R¹ represents a substituted C$_{1-22}$ alkyl of the general formula (IIIa) or (IIIc),

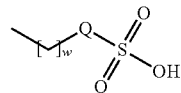

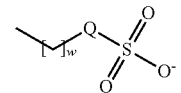

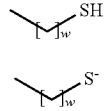

in which Q represents O or CH₂, w represents a number from 1 to 22, q represents 1 or 2 and A⁺ represents a cation selected from alkali metal cations where q=1, ½ alkaline earth cations where q=2 and ammonium ions where q=1, X$^{o-}$ represents an anion selected from F⁻, Cl⁻, Br⁻, I⁻, OH⁻, HSO₃⁻, SO₃²⁻, SO₄²⁻, HSO₄⁻, NO₂⁻, NO₃⁻, PO₄³⁻, HPO₄²⁻, H₂PO₄⁻, BF₄⁻, PF₆⁻, ClO₄⁻, acetate, citrate, formate, glutarate, lactate, malate, malonate, oxalate, pyruvate, tartrate, methanesulfonate, methyl sulfate, p-toluenesulfate and succinate, n is a number from 1 to 5, m is a number from 0 to 4 and o is a number from 1 to 3 and p and r independently of one another represent a number from 0 and 7, with the proviso that the sum of n and the product of p and q is equal to the sum of m and the product of r and o;

wherein the detergent comprises 0.001 wt. % to 10 wt. % of the metal complex of the formula (III).

5. The dishwashing detergent, of claim 4, is an automatic dishwashing detergent.

6. The detergent according to claim 4, wherein the detergent comprises 0.01 wt. % to 3 wt. % of the metal complex of the formula (III).

7. A metal complex of the general formula (III), $$(A^{q+})_p[M^{n+}L^{m-}](X^{o-}),\quad\text{(III)}$$

in which q represents 1 or 2 and A⁺ represents a cation selected from alkali metal cations where q=1, ½ alkaline earth cations where q=2 and ammonium ions where q=1, M$^{n+}$ represents an aluminum ion, a transition metal ion or a lanthanoid metal ion, L represents a ligand of the formula (I)

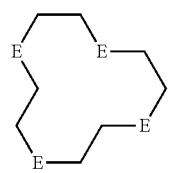

in which each E independently represents O or NR¹, with the proviso that at least 1 E is not O, each R¹ independently represents H, unsubstituted or substituted, linear or branched C$_{1-22}$ alkyl, unsubstituted or substituted, linear or branched C$_{1-22}$ heteroalkyl, unsubstituted or substituted aryl, unsubstituted or substituted heteroaryl, unsubstituted or substituted, linear or branched C$_{2-20}$ alkenyl, unsubstituted or substituted, linear or branched $C_{2-20}$ alkynyl, unsubstituted or substituted, linear or branched $C_{2-20}$ heteroalkenyl, unsubstituted or substituted, linear or branched alkylaryl, or unsubstituted or substituted, linear or branched alkylheteroaryl, with the proviso that at least 1 $R^1$ represents a substituted $C_{1-22}$ alkyl of the general formula (IIa) or (IIc), or with the proviso that at least 1 $R^1$ represents a substituted $C_1$-22 alkyl of the general formula (IIIa) or (IIIc),

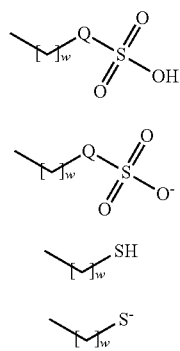

(IIa)

(IIc)

(IIIa)

(IIIc)

in which Q represents O or $CH_2$, w represents a number from 1 to 22, q represents 1 or 2 and $A^+$ represents a cation selected from alkali metal cations where q=1, ½ alkaline earth cations where q=2 and ammonium ions where q=1, $X^{o-}$ represents an anion selected from $F^-$, $Cl^-$, $Br^-$, $I^-$, $OH^-$, $HSO_3^-$, $SO_3^{2-}$, $SO_4^{2-}$, $HSO_4^-$, $NO_2^-$, $NO_3^-$, $PO_4^{3-}$, $HPO_4^{2-}$, $H_2PO_4^-$, $BF_4^-$, $PF_6^-$, $ClO_4^-$, acetate, citrate, formate, glutarate, lactate, malate, malonate, oxalate, pyruvate, tartrate, methanesulfonate, methyl sulfate, p-toluenesulfate and succinate, n is a number from 1 to 5, m is a number from 0 to 4 and o is a number from 1 to 3 and p and r independently of one another represent a number from 0 and 7, with the proviso that the sum of n and the product of p and q is equal to the sum of m and the product of r and o;

wherein in the general formula (I) the groups $R^1$ which do not correspond to the general formula (IIa) or (IIc) are selected from the group consisting of

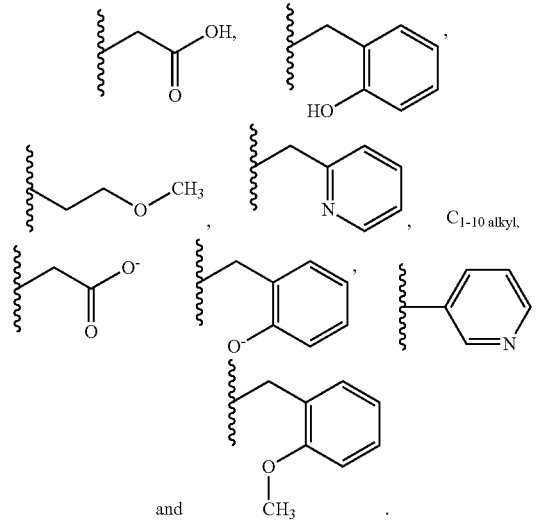

8. The complex according to claim 7, wherein $M^{n+}$ is selected from the group consisting of $Al^{3+}$, $Ti^{4+}$, $Y^{3+}$, $Zr^{4+}$, $La^{3+}$, $Ce^{3+}$, $Ce^{4+}$, $Sc^{3+}$, $Yb^{3+}$, $Ta^{5+}$ and mixtures thereof.

9. The complex according to claim 7 wherein, in the general formula (I), w represents a number from 2 to 20.

10. The complex according to claim 7 wherein, w represents a number from 3 to 18.

* * * * *

UNITED STATES PATENT AND TRADEMARK OFFICE
CERTIFICATE OF CORRECTION

PATENT NO. : 11,702,616 B2
APPLICATION NO. : 17/186406
DATED : July 18, 2023
INVENTOR(S) : Christian Kropf, Sebastian Polarz and Marvin Lionel Frisch It is certified that error appears in the above-identified patent and that said Letters Patent is hereby corrected as shown below:

In the Claims

Column 25, Line 35 change "$(A^{q+})_p[M^{n+}L^{m-}](X^{o-})$" to --$(A^{q+})_p[M^{n+}L^{m-}](X^{o-})_r$--.
Column 25, Line 64 change "$C_1$-22" to --$C_{1-22}$--.
Column 26, Line 43 change "$(A^{q+})_p[M^{n+}L^{m-}](X^{o-})$" to --$(A^{q+})_p[M^{n+}L^{m-}](X^{o-})_r$--.
Column 27, Line 7 change "$C_1$-22" to --$C_{1-22}$--.

Signed and Sealed this
Seventh Day of November, 2023

Katherine Kelly Vidal
*Director of the United States Patent and Trademark Office*